United States Patent [19]
Dassanayake et al.

[11] Patent Number: 5,900,213
[45] Date of Patent: May 4, 1999

[54] USE OF DIAMINES TO DISINFECT AND CLEAN CONTACT LENSES AND PRESERVE OPHTHALMIC COMPOSITIONS

[75] Inventors: Nissanke L. Dassanayake, Arlington; Ronald L. Schlitzer, Fort Worth; Joonsup Park, Arlington; Bahram Asgharian, Fort Worth, all of Tex.

[73] Assignee: Alcon Laboratories, Inc., Fort Worth, Tex.

[21] Appl. No.: 09/047,584

[22] Filed: Mar. 25, 1998

Related U.S. Application Data

[63] Continuation of application No. 08/661,268, Jun. 10, 1996, abandoned, which is a continuation of application No. 08/336,432, Nov. 9, 1994, abandoned, which is a continuation of application No. 08/054,926, Apr. 28, 1993, abandoned.

[51] Int. Cl.$^6$ ...................................................... A61L 2/16
[52] U.S. Cl. ...................... 422/28; 424/78.04; 514/839; 514/840
[58] Field of Search .......................... 422/28; 424/78.04; 514/839, 840, 671, 672, 673, 643; 564/282, 286, 288, 292, 290, 295, 511

[56] References Cited

U.S. PATENT DOCUMENTS

| | | |
|---|---|---|
| 2,759,021 | 8/1956 | Gaar et al. . |
| 3,083,143 | 3/1963 | Schmid et al. . |
| 3,121,115 | 2/1964 | Meuly . |
| 3,206,462 | 9/1965 | McCarty . |
| 3,373,107 | 3/1968 | Rice et al. . |
| 3,418,322 | 12/1968 | Tulagin et al. . |
| 3,534,032 | 10/1970 | Kalopissis . |
| 3,729,564 | 4/1973 | Chang et al. . |
| 3,873,688 | 3/1975 | Kalopissis et al. . |
| 3,891,385 | 6/1975 | Kalopissis et al. . |
| 3,943,255 | 3/1976 | Newkirk . |
| 4,004,030 | 1/1977 | Schwarzmann et al. . |
| 4,029,817 | 6/1977 | Blanco et al. ........................... 424/329 |
| 4,119,668 | 10/1978 | Diana et al. ....................... 260/567.6 P |
| 4,134,971 | 1/1979 | Inoue et al. . |
| 4,185,098 | 1/1980 | Cuntze et al. . |
| 4,407,791 | 10/1983 | Stark ......................................... 424/80 |
| 4,883,917 | 11/1989 | Smith et al. ............................. 564/292 |
| 5,415,837 | 5/1995 | Schafer et al. . |

FOREIGN PATENT DOCUMENTS

| | | |
|---|---|---|
| 1 397 231 | of 1965 | France . |
| 1 024 977 | 2/1958 | Germany . |
| 2 113 208 | 9/1972 | Germany . |
| 26 06 519 | 9/1976 | Germany . |
| 56-2351 | 1/1981 | Japan . |
| 455 522 1961 | of 1961 | Switzerland . |
| 823303 | 11/1959 | United Kingdom . |
| 1 305 502 | 2/1973 | United Kingdom . |
| 93/17723 | 9/1993 | WIPO . |

OTHER PUBLICATIONS

Bass, et al., "Structure–Activity Studies on Inhibition of Streptococcus mutans by Long–Chain Aliphatic Diamines," *Journal of Dental Research*, vol. 54, No. 5, pp. 972–977 (1975).

Block, S., "Disinfection, Sterilization and Preservation, 4th Edition," 1991, Lea & Febiger Philadelphia–London, p. 931.

El Sokkari et al., "Antibacterial activity of some new surfactants," *Chemical Abstracts*, vol. 76, No. 25, Jun. 19, 1972, abstract No. 149460.

Klimm et al., "Effect of locally acting prophylactic anticarious agents on the microflora of dental deposits," *Chemical Abstracts*, vol. 92, No. 23, Jun. 9, 1980, abstract No. 191485.

Powers, et al., "Synthesis and CMC Determination of a Series of Aliphatic Diamines," *Journal of Pharmaceutical Sciences*, vol. 64, No. 5, pp. 883–885 (1975).

Wing et al., "Dissociative effects of a novel immunomodulating agent (CP–20,961) on host defenses of mice," *Chemical Abstracts*, vol. 102, No. 19, May 13, 1985, abstract No. 160169.

*Primary Examiner*—José G. Dees
*Assistant Examiner*—Barbara Badio
*Attorney, Agent, or Firm*—Gregg C. Brown

[57] ABSTRACT

N,N-dialkyl and N'-alkylethylene diamines of the formula:

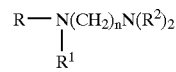

wherein R, $R^1$ and $R^2$ are as described in the specification. The compounds are useful in disinfecting and cleaning contact lenses and preserving ophthalmic products.

10 Claims, No Drawings

USE OF DIAMINES TO DISINFECT AND CLEAN CONTACT LENSES AND PRESERVE OPHTHALMIC COMPOSITIONS

This application is a continuation of U.S. patent application Ser. No. 08/661,268, filed Jun. 10, 1996, now abandoned, which is a continuation of U.S. patent application Ser. No. 08/336,432, filed Nov. 9, 1994, now abandoned, and which is a continuation of U.S. patent application No. 08/054,926, filed Apr. 28, 1993, now abandoned.

BACKGROUND OF THE INVENTION

The present invention relates to the field of ophthalmology. More particularly, the invention is directed to solutions for disinfecting contact lenses, and to the chemical preservation of various types of ophthalmic products.

Contact lenses are exposed to a broad spectrum of microbes during normal wear and become soiled relatively quickly. Routine cleaning and disinfecting of the lenses are therefore required. Although the frequency of cleaning and disinfecting may vary somewhat among different types of lenses and lens care regimens, daily cleaning and disinfecting is normally required. Failure to clean and disinfect the lens properly can lead to a multitude of problems ranging from mere discomfort when the lenses are being worn to serious ocular infections. Ocular infections caused by particularly virulent microbes, such as *pseudomonas aeruginosa*, can lead to loss of the infected eye(s) if left untreated or if allowed to reach an advanced stage before treatment is initiated. It is therefore extremely important that patients disinfect their contact lenses in accordance with the regimen prescribed by their optometrist or ophthalmologist.

Unfortunately, patients frequently fail to follow the prescribed regimens. Many patients find regimens to be difficult to understand and/or complicated, and as a result do not comply with one or more aspects of the regimen. Other patients may have a negative experience with the regimen, such as ocular discomfort attributable to the disinfecting agent, and as a result do not routinely disinfect their lenses or otherwise stray from the prescribed regimen. In either case, the risk of ocular infections is exacerbated.

Despite the availability of various types of contact lens disinfecting systems, such as heat, hydrogen peroxide, and other chemical agents, there continues to be a need for improved systems which: 1) are simple to use, 2) have potent antimicrobial activity, and 3) are nontoxic (i.e., do not cause ocular irritation as the result of binding to the lens material). The present invention is directed to meeting this need.

SUMMARY OF THE INVENTION

The present invention is directed to certain novel N,N-dialkyl, N'-alkyl, ethylene diamines, and to the use of these compounds and related compounds to disinfect contact lenses and to preserve ophthalmic preparations. The invention is also directed to contact lens disinfecting compositions which contain one or more of the subject compounds, and to various types of ophthalmic compositions (e.g., pharmaceuticals, artificial tears and comfort drops) which contain the compounds for purposes of preserving the compositions against microbial contamination.

In addition to having antimicrobial activity, including both antibacterial and antifungal activity, the compounds of the present invention are also surface active. As a result, the compounds also help to clean contact lenses by facilitating the removal of deposits from the lenses.

The diamines of the present invention retain their antimicrobial activity in the presence of $Na^+$, $Ca^{++}$, $Cl^-$ and other inorganic ions produced by the dissociation of alkaline and alkaline earth metal salts (e.g., sodium chloride and calcium chloride), and are compatible with polymers and surfactants frequently used in ophthalmic products, such as polyvinylpyrrolidone, and polyoxyethylene/polyoxypropylene copolymers of ethylene diamines. In fact, it has been determined that the presence of sodium chloride may actually enhance the antimicrobial activity of the diamines of the present invention. These properties represent significant advantages, relative to many of the antimicrobial agents previously used in the ophthalmic field.

DESCRIPTION OF PREFERRED EMBODIMENTS

The compounds used in the present invention comprise one or more compounds of the following formula, or pharmaceutically acceptable salts thereof (e.g., hydrohalide salts):

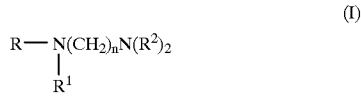

(I)

wherein: R is $C_6$–$C_{18}$ saturated or unsaturated alkyl, alkylaryl, or alkoxyaryl;

$R^1$ is hydrogen, or $C_1$–$C_{18}$ saturated or unsaturated alkyl, alkylaryl, alkoxyaryl, or alkanol;

n is 2 to 16, preferably 2 to 4; and $R^2$ is $C_1$–$C_8$ saturated or unsaturated alkyl or alkanol. The compounds wherein $R^2$ is ethyl are particularly preferred, as are the following compounds:

| Compound No. | R | $R^1$ | n | $R^2$ |
|---|---|---|---|---|
| 1 | Dodecyl | H | 2 | Ethyl |
| 2 | Tetradecyl | H | 2 | Ethyl |
| 3 | Hexadecyl | H | 2 | Ethyl |
| 4 | Oleyl | H | 2 | Ethyl |
| 5 | Stearyl | H | 2 | Ethyl |
| 6 | Dodecyl | H | 3 | Methyl |
| 7 | Tetradecyl | H | 3 | Methyl |
| 8 | Hexadecyl | H | 3 | Methyl |
| 9 | Oleyl | H | 3 | Methyl |
| 10 | Stearyl | H | 3 | Methyl |
| 11 | Oleyl | H | 2 | $CH_2CH_2OH$ |
| 12 | Oleyl | H | 3 | $CH_2CH_2OH$ |
| 13 | Oleyl | $CH_2CH_2OH$ | 2 | $CH_2CH_2OH$ |
| 14 | Oleyl | $CH_2CH_2OH$ | 3 | $CH_2CH_2OH$ |

The most preferred compound is N,N-diethyl-N'-oleyl ethylene diamine (i.e., Compound No. 4), which has the following general formula:

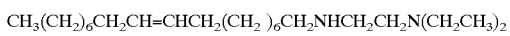

The compounds of the present invention can be synthesized in accordance with the following reaction scheme:

1. oleic acid→oleoyl chloride
2. oleoylchloride+$NH_2CH_2CH_2N(C_2H_5)_2$→oleoyl-$NHCH_2CH_2N(C_2H_5)_2$
3. oleoyl-$NHCH_2CH_2N(C_2H_5)_2$→Oleyl-$NHCH_2CH_2N(C_2H_5)_2$ The starting materials for the synthesis of the target compounds are readily available commercially (e.g., from Aldrich Chemical Company, Milwaukee, Wis.). The corresponding acid halide is reacted with the corresponding amine to provide the amide. The amide is reduced with lithium aluminum hydride to the desired amine. The purification is performed either by high vacuum distillation or by column chromatography (with silica gel as a support). These compounds are characterized by gas chromatography, infrared, nuclear magnetic resonance spectra, and elemental analysis.

The compounds of formula (I) wherein $R_2$ is methyl or hydroxyethyl are known. Such compounds are described in the following articles: Bass, et al., *Journal of Dental Research*, volume 54, number 5, pages 972–977 (1975); and Powers, et al., *Journal of Pharmaceutical Sciences*, volume 64, number 5, pages 883–885 (1975). The entire contents of both of these articles are hereby incorporated in the present specification by reference. The above-cited articles do not describe the use of compounds of formula (I) as disinfectants or preservatives in ophthalmic products, particularly products used in the care of contact lenses.

The compounds of formula (I) can be used individually, in combination with one or more other compounds of formula (I), or in combination with other disinfectants or preservatives. The compounds may, for example, be used in combination with the polymeric quaternary ammonium compounds described in U.S. Pat. No. 4,407,791; the entire contents of that patent are hereby incorporated in the present specification by reference. As described in the '791 patent, those polymeric quaternary ammonium compounds are useful in disinfecting contact lenses and preserving ophthalmic compositions.

The amount of each compound used will depend on the purpose of the use, e.g., disinfection of contact lenses or preservation of ophthalmic products, and the absence or inclusion of other antimicrobial agents. The concentrations determined to be necessary for the above-stated purposes can be functionally described as "an amount effective to disinfect" and "an amount effective to preserve" or variations thereof. The concentrations used for disinfection will generally be in the range of from about 0.0001 to about 0.1 percent by weight based on the total weight of the composition ("wt. %"). The concentrations used for preservation will generally be in the range of from about 0.00001 to about 0.01 wt. %.

The compounds of formula (I) may be included in various types of ophthalmic compositions as preservatives, so as to prevent microbial contamination of the compositions. The types of compositions which may be preserved by the compounds of formula (I) include: ophthalmic pharmaceutical compositions, such as topical compositions used in the treatment of glaucoma, infections, allergies or inflammation; compositions for treating contact lenses, such as cleaning products and products for enhancing the ocular comfort of patients wearing contact lenses; ana various other types of compositions, such as ocular lubricating products, artificial tears, astringents, and so on. The compositions may be aqueous or nonaqueous, but will generally be aqueous. As will be appreciated by those skilled in the art, the compositions may contain a wide variety of ingredients, such as tonicity agents (e.g., sodium chloride or mannitol), surfactants (e.g., polyvinyl pyrrolidone and polyoxyethylene/ polyoxypropylene copolymers), viscosity adjusting agents (e.g., hydroxypropyl methyl cellulose and other cellulose derivatives) and buffering agents (e.g., borates, citrates, phosphates and carbonates). The present invention is not limited with respect to the types of ophthalmic compositions in which the compounds of formula (I) may be contained as preservatives. In fact, as already noted above, the compatibility of the compounds of formula (I) with other ingredients of ophthalmic compositions, such as inorganic ions, polymers and surfactants, is a distinct advantage of the present invention, relative to antimicrobial agents previously utilized in the ophthalmic field.

As with the ophthalmic compositions of the present invention which contain one or more compounds of formula (I) as preservatives, the form of the compositions of the present invention containing one or more of the compounds for purposes of disinfecting contact lenses is not limited. The contact lens disinfecting compositions of the present invention will preferably be formulated as aqueous solutions, but may also be formulated as nonaqueous solutions, as well as suspensions, gels, and so on. The compositions may contain a variety of tonicity agents, surfactants, viscosity adjusting agents and buffering agents, as described above. The chemical compatibility of the compounds of formula (I) is also a significant advantage with respect to the use of these compounds in the contact lens disinfecting compositions of the present invention.

The above-described compositions may be used to disinfect contact lenses in accordance with processes known to those skilled in the art. More specifically, the lenses will first be removed from the eyes of the patients, and then will be immersed in the compositions for a time sufficient to disinfect the lenses. This immersion will typically be accomplished by means of soaking the lenses in a solution overnight (i.e., approximately six to eight hours). The lenses will then be rinsed and placed in the eye. Prior to immersion in the disinfecting compositions, the lenses will preferably also be cleaned and rinsed.

The compounds of formula (I) also have surface active properties. As a result of these properties, the compounds are also useful in cleaning contact lenses. More specifically, the surfactant properties of the compounds facilitate the removal of deposits typically accumulated on contact lenses when worn by human patients. These deposits vary from patient to patient, but will typically include proteins, lipids, polysaccharides and mixtures thereof, as well as various other soils which may accumulate on the lenses during normal wear and handling. The compounds will exhibit some cleaning effect even at the relatively low concentrations required for purposes of preserving ophthalmic compositions or disinfecting contact lenses. This cleaning effect is therefore useful as a supplement to the effect of other cleaning agents which may be contained in the compositions, such as anionic or nonionic surfactants. Moreover, when used at a concentration of 0.01 wt. % or higher, the compounds exhibit a more pronounced cleaning effect. The manner in which the cleaning effect of the compounds of formula (I) is utilized will depend on the type of contact lens being treated, the severity and type of the deposits on the lenses, and the overall treatment regimen used by the patient. The selection of other components for inclusion in the contact lens cleaning compositions of the present invention will also depend on these factors. The cleaning compositions will generally contain one or more of the compounds of formula (I) in an amount of at least 0.01 wt. %, and preferably from about C.01 to 1.0 wt. %.

The above-described compositions may be used to clean contact lenses in accordance with known processes. For example, the lenses, after first being removed from the eye and preferably also rinsed, may be lightly rubbed with a small amount of the compositions between the fingers, or may be immersed in a somewhat larger volume of the compositions and then allowed to soak. The lenses are then rinsed and disinfected before being replaced in the eyes of the patients.

All of the above-described compositions will be formulated so as to be compatible with the eye and/or contact lenses to be treated with the compositions. As will be appreciated by those skilled in the art, the ophthalmic compositions intended for direct application to the eye will be formulated so as to have a pH and tonicity which are compatible with the eye. This will normally require a buffer to maintain the pH of the composition at or near physiologic pH (i.e., 7.4) and may require a tonicity agent to bring the osmolality of the composition to a level at or near 300–320 milliosmoles. The formulation of compositions for disinfecting and/or cleaning contact lenses will involve similar considerations, as well as considerations relating to the physical effect of the compositions on contact lens materials and the potential for binding or absorption of the components of the composition by the lens.

The compositions and methods of the present invention may be used in conjunction with various types of contact lenses, including both lenses generally classified as "hard" and lenses generally classified as "soft".

The following examples are presented to further illustrate methods of synthesizing the novel diamines of the present invention:

EXAMPLE 1
N,N-diethyl-N'-octylethylenediamine

A mixture of N,N-diethylethylenediamine (9.6 g, 0.0826 mol) and 8.4 g (0.0826 mol) of triethylamine in 40 ml of chloroform was added dropwise to the ice cold chloroform solution (40 ml) of octanoyl chloride (13.4 g, 0.0826 mol). After addition, the ice bath was removed and the solution was stirred for 5 hours at room temperature. The reaction mixture was stirred with aqueous sodium bicarbonate for one hour. The organic layer was then dried over magnesium sulfate leaving a yellow liquid which was concentrated in vacuo. The yellow liquid was subject to high vacuum distillation to yield 9.65 g (0.040 mol, 48.3%, b.p.$_{0.05mm}$=115° C.). The above amide (9.65 g, 0.040 mol) was reduced with lithium aluminum hydride (1.7 g, 0.045 mol) to yield 6.94 g (0.030 mol, 76.1%) of the product after vacuum distillation: (b.p.$_{0.05mm}$=77° C.). NMR (CDCl$_3$) δ 2.7–2.4 (m, 10H, NCH$_2$ and NHC$\underline{H}_2$), 1.6 (s, 1H, NH), 1.5 (m, 2H, NHCH$_2$C$\underline{H}_2$), 1.28 (s, 10H, NHCH$_2$CH$_2$(C$\underline{H}_2$)$_5$), 1.01 (t, 6H, NCH$_2$C$\underline{H}_3$), 0.88 (t, 3H, CH$_3$). Elemental Analysis: Calcd. for C$_{14}$H$_{32}$N$_2$(228.41): C, 73.61; H, 14.12; N, 12.26. Found: C, 73.68; H, 14.76; N, 12.12.

EXAMPLE 2
N-n-dodecyl-N'N'-diethylethylenediamine 5.12 g (23.4 mmol) of lauroyl chloride and 3.41 g (29.3 mmol) of N,N-diethylethylenediamine were reacted in dry chloroform. The reaction mixture was concentrated by evaporation of chloroform and treated with sodium bicarbonate in a mixture of ethanol and water. Following extraction with chloroform, the combined chloroform extracts were dried and concentrated, upon which the amide began to crystallize. Without further purification, the amide was reduced with lithium aluminum hydride in THF using standard procedures. After quenching and filtration of the reaction mixture, the filtrate was dried and concentrated then distilled under reduced pressure to yield 2.29 g (34%) of the diamine (bp 115–119°, 20 v). Purity by GC>99%.

$^1$H NMR (CDCl$_3$, 200 MHz) δ 2.68–2.40 (m, 10H, —C$\underline{H}_2$NHC$\underline{H}_2$CH$_2$N(C$\underline{H}_2$CH$_2$)$_2$), 1.45 (m, 2H, —CH$_2$C$\underline{H}_2$CH$_2$NH), 1.25 (s, 18H, CH$_3$(C$\underline{H}_2$)$_9$—), 1.10 (t, 6H, N(CH$_2$C$\underline{H}_3$)$_2$), 0.85 (t, 3H, CH$_3$).

EXAMPLE 3
N-Tetradecyl-N',N',-diethylethylenediamine

A mixture of N,N-diethylethylenediamine (5.8 g. 0.05 mole) and triethylamine (5 g.) in 250 ml of chloroform was cooled on ice bath and reacted with 12.3 g (0.05 mol) of myristoyl chloride by adding dropwise. The reaction temperature was maintained below 10° C. After the completion of the addition, the ice bath was removed and the reaction mixture was refluxed for two hours. The reaction mixture was stirred with NaHCO$_3$ at room temperature for one hr. and the chloroform layer was washed with NaHCO$_3$ saturated solution and dried with MgSO$_4$. The concentration in vacuo yielded a crystalline material of 14 g. (86%). Nmr spectra, IR, and GC confirmed the structure of the above compound.

This amide (10 g, 0.03 mol) was reduced with lithium aluminum hydride (1.2 g.) in 200 ml of tetrahydrofuran solvent to yield 8 g. (84%) of the diamine after high vacuum distillation (b.p.$_{0.01}$=135–140° C.). Nmr (CDCl$_3$) 2.7–2.45 (m, 10, N—CH$_2$), 1.7 (br, 1, NH), 1.5 (m, 2, N—CH$_2$CH$_2$), 1.3 (app. s, 22, CH$_2$), 1.0 (t, 6, NCH$_2$CH$_2$), and 0.9 (t, 3, CH$_3$). Elemental Analysis: Calcd. for C20H44N2 (312.58): C, 76.85; H, 14.19; N, 8.96 Found: C, 76.78; H, 14.37; N, 8.96.

EXAMPLE 4
N,N-diethyl-N'-oleylethylenediamine 11.37 g (30.0 mmol) of N,N-diethyl-N'-oleoylethylenediamine was reduced with lithium aluminum hydride in THF using standard procedures. After quenching and filtration of the reaction mixture, the filtrate was dried and concentrated then redissolved in ethanol and acidified with HCl. The salt was recrystallized twice from ethyl acetate, affording 9.84 g (75%) of the diamine. Purity by GC, 92.5%. Anal. calcd. for C$_{24}$H$_{52}$Cl$_2$N$_2$: C, 65.58; H, 1192: N, 6.37. Found: C, 65.50; H, 11.75; N, 6.35.

$^1$H NMR (CDCl$_3$, 200 MHz) δ 5.34 (t, 2H, CH=), 3.92 (q, 2H, NCC$\underline{H}_2$CH$_2$—N), 3.46 (t, 2H, NHCH$_2$C$\underline{H}_2$—N), 3.27 (q, 4H, N(C$\underline{H}_2$CH$_3$)$_2$), 3.00 (q, 2H, —CH$_2$CH$_2$C$\underline{H}_2$—N), 2.10 (q, 4H, C$\underline{H}_2$CH=), 1.85 (m, 2H, —CH$_2$C$\underline{H}_2$CH$_2$—N), 1.50 (t, 6H, N(CH$_2$C$\underline{H}_3$), 1.27 (s, 22H, —C$\underline{H}_2$—), 0.88 (t, 3H, CH$_3$).

EXAMPLE 5
N-(3,5-di-t-butylbenzyl)-N',N'-diethylethylenediamine

This compound was prepared by chlorination of 3,5-di-t-butylbenzoic acid with thionyl chloride using standard procedures to give 3,5-di-t-butylbenzoyl chloride. 3.26 g (12.9 mmol) of the chloride was then reacted with 1.95 g (16.8 mmol) of N,N-diethylethylenediamine in dry chloroform. The reaction mixture was concentrated by evaporation of chloroform and treated with sodium bicarbonate in a mixture of ethanol and water. Following extraction with chloroform, the combined chloroform extracts were dried and concentrated, upon which the amide began to crystallize. Without further purification, the amide was reduced with lithium aluminum hydride in THF using standard procedures. After quenching and filtration of the reaction mixture, the filtrate was dried and concentrated then distilled under reduced pressure to yield 2.00 g (49%) of the diamine. (bp 105–108°, 10 v). Purity by GC>99%.

$^1$H NMR (CDCl$_3$, 200 MHz) δ 7.30–7.15 (2 s, 3H, —C$_6$$\underline{H}_3$—), 3.79 (s, 2H, C$_6$—C$\underline{H}_2$—), 2.70 (t, 2H, NHC$\underline{H}_2$CH$_2$—N), 2.50 (q, 4H, N(C$\underline{H}_2$CH$_3$)$_2$), 1.32 (s, 18H, —C(CH$_3$)$_3$), 1.00 (t, 6H, CH$_3$).

The following examples are presented to further illustrate ophthalmic compositions which may contain one or more of the compounds of formula (I):

EXAMPLE 6

The following formulation might serve as a vehicle for an ophthalmic drug. The formulation would contain one or more compounds of formula (I) as a preservative.

| Ingredient | Amount (wt. %) |
| --- | --- |
| Sodium Chloride | 0.5% |
| Mannitol | 2.5% |
| HEPES | 0.119% |
| NaOH/HCl | pH 7.0 |
| Purified water | QS 100 |

EXAMPLE 7

The following formulation may be utilized as a contact lens disinfecting solution. The formulation would contain one or more compounds of formula (I) as a disinfectant.

| Ingredient | Amount (wt. %) |
| --- | --- |
| Mannitol | 0.64% (w/v) |
| Boric Acid | 0.225% |
| Sodium Borate | 0.08% |
| Sodium Citrate | 0.46% |
| Citric Acid | 0.016% |
| Sodium Chloride | 0.48% |
| Disodium Edetate | 0.05% |
| NaOH/HCl | pH 7.0 |
| Purified Water | QS 100 |

EXAMPLE 8

The following formulation may be utilized as a contact lens disinfecting solution, and would also aid in the cleaning of the lens.

| Ingredient | Amount (wt. %) |
| --- | --- |
| Compound No. 4 | 0.01% |
| Boric Acid | 0.58% |
| Sodium Borate | 0.18% |
| Sodium Chloride | 0.49% |
| Disodium Edetate | 0.05% |
| Polaxomine | 0.1% |
| NaOH/HCl | pH 7.0 |
| Purified Water | QS 100% |

What is claimed is:

1. A method of disinfecting a contact lens which comprises immersing the lens in an antimicrobial composition for a time sufficient to disinfect the lens, said composition comprising an amount of a compound of the following formula effective to disinfect the lens:

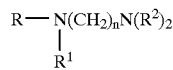

wherein R is $C_6$–$C_{18}$ saturated or unsaturated alkyl, alkylaryl or alkoxyaryl;

$R^1$ is hydrogen, or $C_1$–$C_{18}$ saturated or unsaturated alkyl, alkylaryl, alkoxyaryl, or hydroxyalkyl; n is 2 to 16; and $R^2$ is $C_1$–$C_8$ saturated or unsaturated alkyl or hydroxyalkyl, or a pharmaceutically acceptable salt thereof; and a pharmaceutically acceptable vehicle therefor.

2. A method according to claim 1, wherein n is 2 to 4.

3. A method according to claim 1, wherein R is selected from oleyl, dodecyl, tetradecyl, hexadecyl and stearyl; $R^1$ is selected from hydrogen and hydroxyethyl; and $R^2$ is selected from methyl, ethyl and hydroxyethyl.

4. A method according to claim 1, wherein R is oleyl, $R^1$ is hydrogen, n is 2, and $R^2$ is ethyl.

5. A method of preserving an ophthalmic composition which comprises including in the composition an amount of a compound of the following formula effective to preserve the composition from microbial contamination:

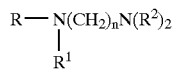

wherein R is $C_6$–$C_{18}$ saturated or unsaturated alkyl, alkylaryl or alkoxyaryl;

$R^1$ is hydrogen, or $C_1$–$C_{18}$ saturated or unsaturated alkyl, alkylaryl, alkoxyaryl, or hydroxyalkyl; n is 2 to 16; and $R^2$ is $C_1$–$C_8$ saturated or unsaturated alkyl or hydroxyalkyl, or a pharmaceutically acceptable salt thereof.

6. A method according to claim 5, wherein n is 2 to 4.

7. A method according to claim 5, wherein R is selected from oleyl, dodecyl, tetradecyl, hexadecyl and stearyl; $R^1$ is selected from hydrogen and hydroxyethyl; and $R^2$ is selected from methyl, ethyl and hydroxyethyl.

8. A method according to claim 5, wherein R is oleyl, $R^1$ is hydrogen, n is 2, and $R^2$ is ethyl.

9. A method of cleaning a contact lens which comprises contacting the surfaces of the lens with a composition comprising an amount of a compound of the following formula effective to clean the lens:

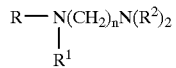

wherein R is $C_6$–$C_{18}$ saturated or unsaturated alkyl, alkylaryl or alkoxyaryl;

$R^1$ is hydrogen, or $C_1$–$C_{18}$ saturated or unsaturated alkyl, alkylaryl, alkoxyaryl, or hydroxyalkyl; n is 2 to 16; and $R^2$ is $C_1$–$C_8$ saturated or unsaturated alkyl or alkanol, or a pharmaceutically acceptable salt thereof; and a pharmaceutically acceptable vehicle therefor.

10. A method according to claim 9, wherein the concentration of said compound is at least 0.01 wt. %.

* * * * *